United States Patent
Yacoubian

(10) Patent No.: US 10,254,252 B2
(45) Date of Patent: Apr. 9, 2019

(54) SURFACE AND SUBSURFACE DETECTION SENSOR

(71) Applicant: Araz Yacoubian, Carlsbad, CA (US)

(72) Inventor: Araz Yacoubian, Carlsbad, CA (US)

(73) Assignee: Ler Technologies, Inc., Encinitas, CA (US)

( * ) Notice: Subject to any disclaimer, the term of this patent is extended or adjusted under 35 U.S.C. 154(b) by 278 days.

(21) Appl. No.: 14/339,187

(22) Filed: Jul. 23, 2014

(65) Prior Publication Data

US 2015/0029819 A1    Jan. 29, 2015

Related U.S. Application Data

(60) Provisional application No. 61/857,391, filed on Jul. 23, 2013.

(51) Int. Cl.
| | | |
|---|---|---|
| G01N 29/24 | (2006.01) | |
| G01N 21/17 | (2006.01) | |
| G01N 21/95 | (2006.01) | |
| G01N 29/04 | (2006.01) | |

(52) U.S. Cl.
CPC ....... *G01N 29/2418* (2013.01); *G01N 21/171* (2013.01); *G01N 21/1717* (2013.01); *G01N 21/9501* (2013.01); *G01N 21/9505* (2013.01); *G01N 29/043* (2013.01); *G01N 2291/263* (2013.01)

(58) Field of Classification Search
CPC .......... G01H 9/00; G01N 21/88; G01N 29/24; G01N 21/171; G01N 21/1717; G01N 21/9501; G01N 29/043; G01N 29/2418; G01N 21/9505; G01N 2291/263
See application file for complete search history.

(56) References Cited

U.S. PATENT DOCUMENTS

| | | | | |
|---|---|---|---|---|
| 4,572,949 A * | 2/1986 | Bowers | ................. | G01H 9/006 250/227.27 |
| 6,154,259 A * | 11/2000 | Hargis | ................. | H04N 5/7416 348/756 |
| 6,216,540 B1 * | 4/2001 | Nelson | ................. | A61B 5/0091 73/633 |
| 6,269,198 B1 * | 7/2001 | Hodgson | ................. | G01H 9/004 356/478 |
| 6,369,379 B1 * | 4/2002 | Kley | ..................... | B82Y 20/00 250/234 |
| 7,256,895 B2 * | 8/2007 | Castonguay | ......... | G01N 21/474 356/446 |
| 7,397,596 B2 * | 7/2008 | Yacoubian | ......... | G01N 21/1717 359/290 |
| 7,463,364 B2 * | 12/2008 | Yacoubian | ......... | G01N 29/2418 356/502 |

(Continued)

OTHER PUBLICATIONS

Nakano; Visualization of high-frequency surface acoustic wave propagation using stroboscopic phase-shift interferometry (Year: 1997).*

*Primary Examiner* — Isam A Alsomiri
*Assistant Examiner* — Amie M Ndure
(74) *Attorney, Agent, or Firm* — James R. McDaniel

(57) ABSTRACT

A sensor can include a plurality of imaging components configured to perform (1) subsurface imaging by acoustical excitation and optical detection, and (2) interferometric surface topographic measurement.

21 Claims, 16 Drawing Sheets

(56) References Cited

U.S. PATENT DOCUMENTS

| | | | | |
|---|---|---|---|---|
| 7,602,501 | B2 * | 10/2009 | Ralston | G01N 21/4795 |
| | | | | 356/497 |
| 7,631,839 | B1 * | 12/2009 | Duncan | B64G 1/105 |
| | | | | 244/158.1 |
| 7,738,092 | B1 * | 6/2010 | Stokowski | G01N 21/95607 |
| | | | | 356/237.2 |
| 8,599,649 | B1 * | 12/2013 | Antonelli | G01H 9/00 |
| | | | | 367/149 |
| 8,797,828 | B1 * | 8/2014 | Lev | G01V 8/00 |
| | | | | 356/486 |
| 2004/0165189 | A1 * | 8/2004 | Castonguay | G01N 21/474 |
| | | | | 356/446 |
| 2005/0207160 | A1 * | 9/2005 | Babayoff | G02B 21/0032 |
| | | | | 362/259 |
| 2005/0280830 | A1 * | 12/2005 | Rembe | G02B 21/0056 |
| | | | | 356/511 |
| 2007/0121115 | A1 * | 5/2007 | Hill | G01N 21/45 |
| | | | | 356/450 |
| 2008/0140341 | A1 * | 6/2008 | Ralston | G01N 21/4795 |
| | | | | 702/155 |
| 2009/0310087 | A1 * | 12/2009 | Itoh | G02B 27/48 |
| | | | | 353/38 |
| 2011/0129955 | A1 * | 6/2011 | Gambino | H01L 27/14627 |
| | | | | 438/70 |

\* cited by examiner

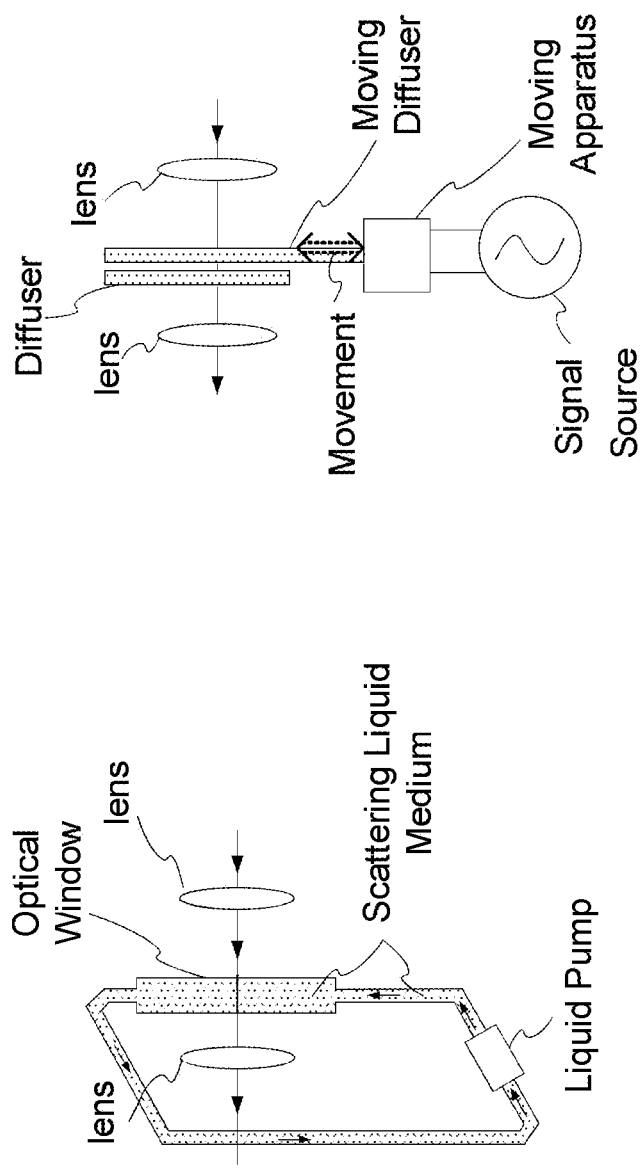

SURFACE AND SUBSURFACE DETECTION SENSOR

RELATED ART

This application incorporates herein by reference in its entirety:
1. U.S. Pat. No. 7,397,596 B2 entitled, "Surface and Subsurface Detection Sensor" naming Araz Yacoubian as inventor and issued on Jul. 8, 2008.
2. U.S. Pat. No. 7,463,364 B2 entitled, "Electro-Optic Sensor" naming Araz Yacoubian as inventor and issued on Dec. 9, 2008.
3. U.S. patent application Ser. No. 11/733,540 entitled, "High Resolution Optical Imager", naming Araz Yacoubian as inventor and filed on Apr. 10 2007.

BACKGROUND OF THE INVENTION

Various methods and apparatus' to produce surface and sub-surface images are described herein. Imaging of sub-surface features and defects is sometimes called depth imaging or depth measurement as described herein. Surface imaging is sometimes referenced as surface topographic imaging or surface metrology throughout this application.

In various parts of this application, x and y dimensions refer to the sample or object surface, specifically the in-plane dimension.

SUMMARY

In an illustrative embodiment, a sensor can include a plurality of imaging components configured to perform (1) subsurface imaging by acoustical excitation and optical detection, and (2) interferometric surface topographic measurement.

BRIEF DESCRIPTION OF THE DRAWINGS

Embodiments relating to both structure and method of operation, may best be understood by referring to the following description and accompanying drawings:

FIGS. 6A, 6B, 6C, 6D, 6E, and 6F are schematic pictorial diagrams showing variations of an apparatus that uses a moving diffuser in the light path when the light source is a coherent or a partially coherent source as shown in FIG. 5 in a manner that reduces or minimizes the effect of speckle pattern when a coherent source is used.

DETAILED DESCRIPTION OF THE EMBODIMENTS

Surface and Subsurface Imaging

Figure 1:
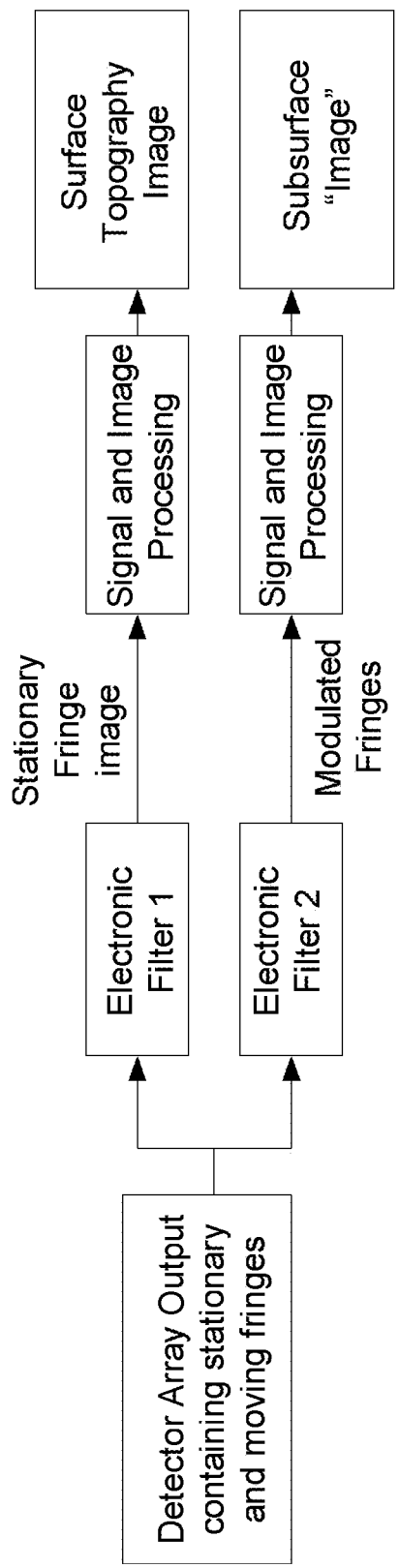
FIG. 1 is a schematic block diagram showing the signal flow to yield surface and subsurface images.

Referring to FIG. 1, a schematic block diagram shows the signal flow to yield surface and subsurface images. The detector array of an interferometric microscope combined with acoustic excitation and detection apparatus produces two-dimensional fringe pattern. Fringes in the fringe pattern either are stationary, moving (i.e. modulated), or both, depending on the surface and subsurface features. The stationary component of the fringes represents surface topography, whereas the modulated part of the fringes represents the subsurface features, as described in Yacoubian (U.S. Pat. No. 7,397,596 B2). The detector array output is split into two, and electronically filtered to produce stationary and moving fringe patterns. After processing the fringe patterns, surface topography image and subsurface image are obtained. Example of Filter 1 is a low-pass filter. Example of Filter 2 is a high-pass or band-pass filter.

Figure 2A:
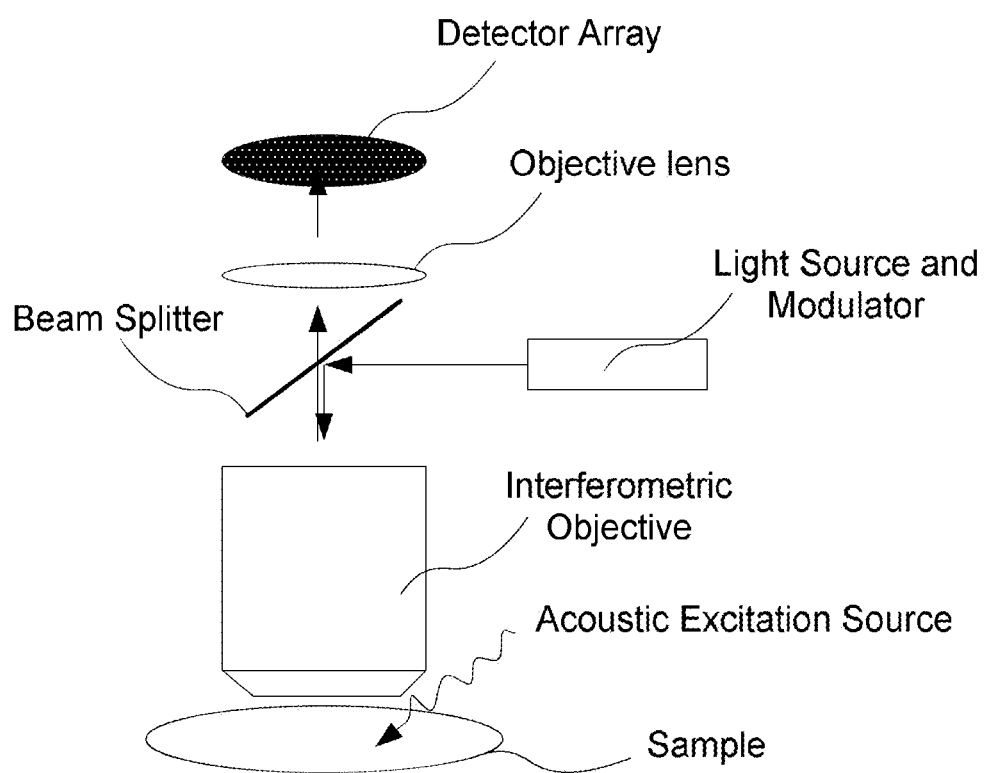
FIGS. 2A, 2B, and 2C are schematic block and pictorial diagrams depicting an apparatus that uses interferometric objective-based microscope combined with an acoustic excitation source to yield surface and subsurface images.
Figure 2B:
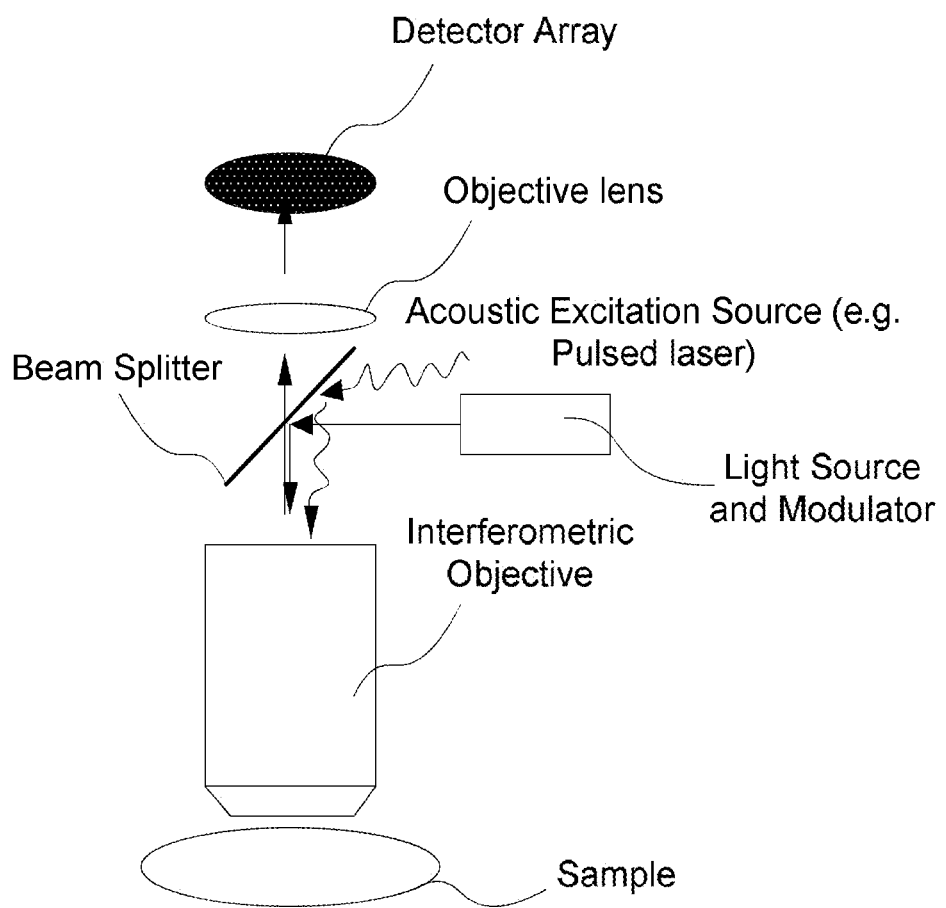
Figure 2C:
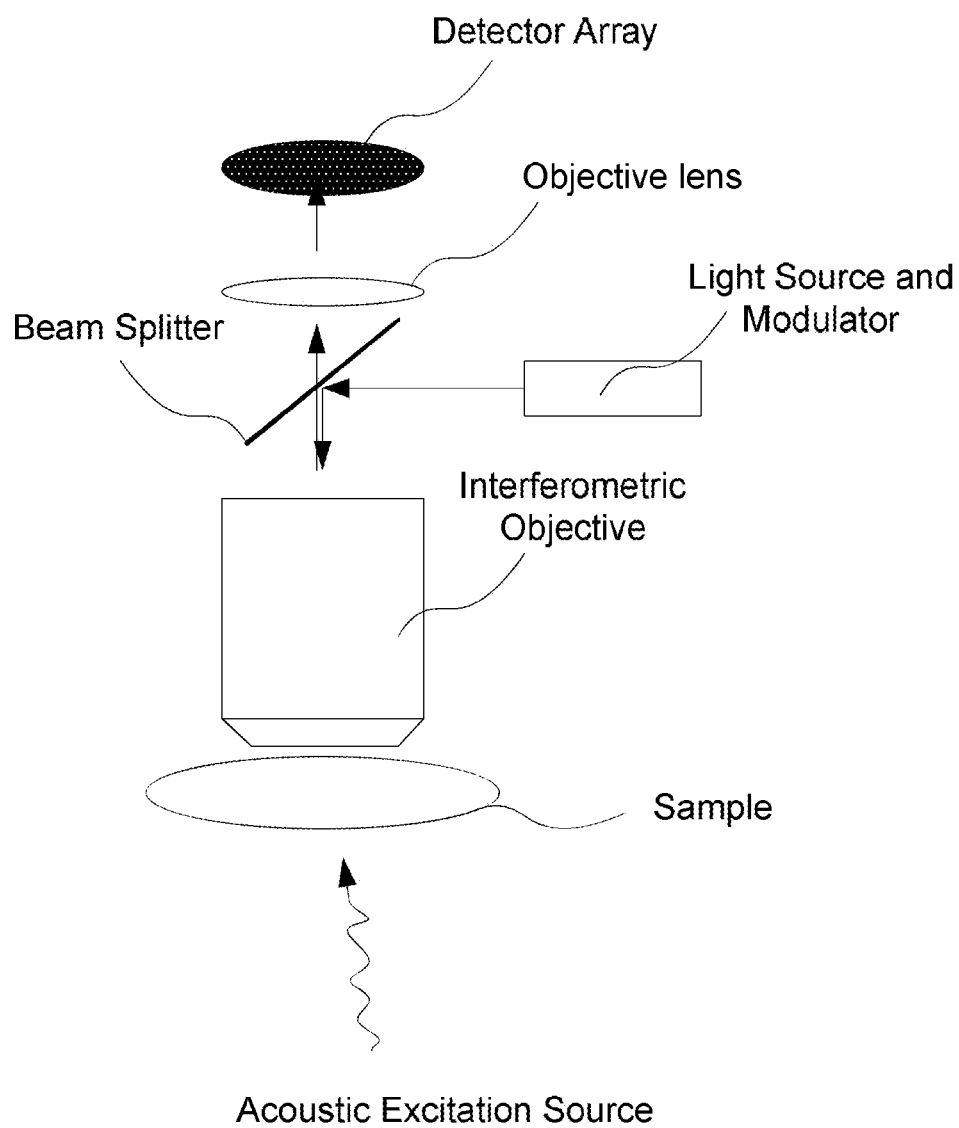

Referring to FIGS. 2A, 2B, and 2C, a schematic block and pictorial diagram that depicts an apparatus that uses interferometric objective-based microscope combined with an acoustic excitation source to yield surface and subsurface images. The output of the array detector is processed as described in FIG. 1. FIGS. 2A, 2B, and 2C show various examples of acoustic excitation methods by illuminating the sample with a pulsed laser. FIGS. 2A and 2B show front side illumination, and FIG. 2C depicts back side illumination of the sample with a pulsed laser. The light source and modulator in the examples are either a single modulator, or a direct modulated laser, while light, broadband, or superluminescence source.

Figure 3A:
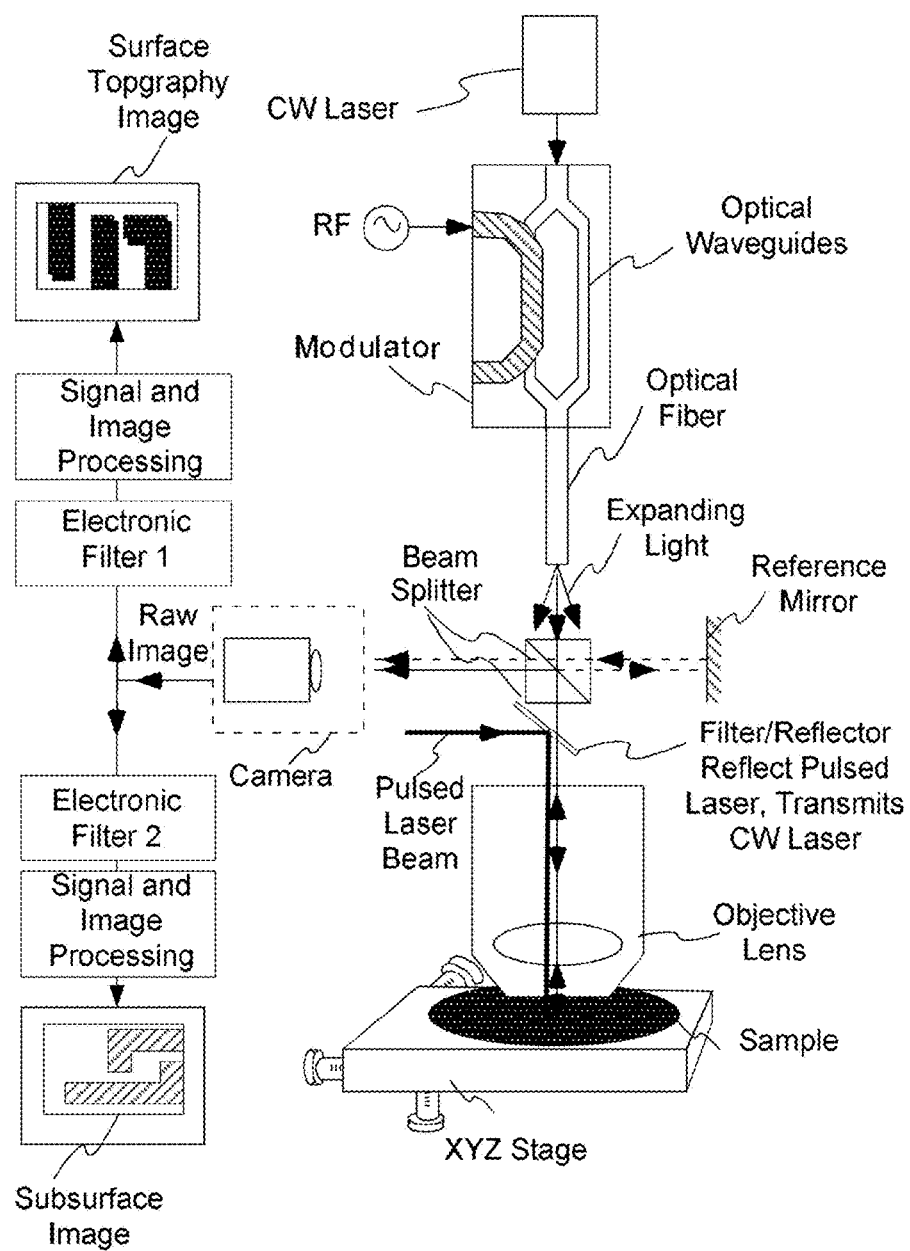
FIGS. 3A, 3B, and 3C are schematic block and pictorial diagrams showing an interferometric microscope apparatus similar to what is described in Yacoubian (U.S. Pat. No. 7,397,596 B2), in which the output of the detector array is processed as described in FIG. 1.
Figure 3B:
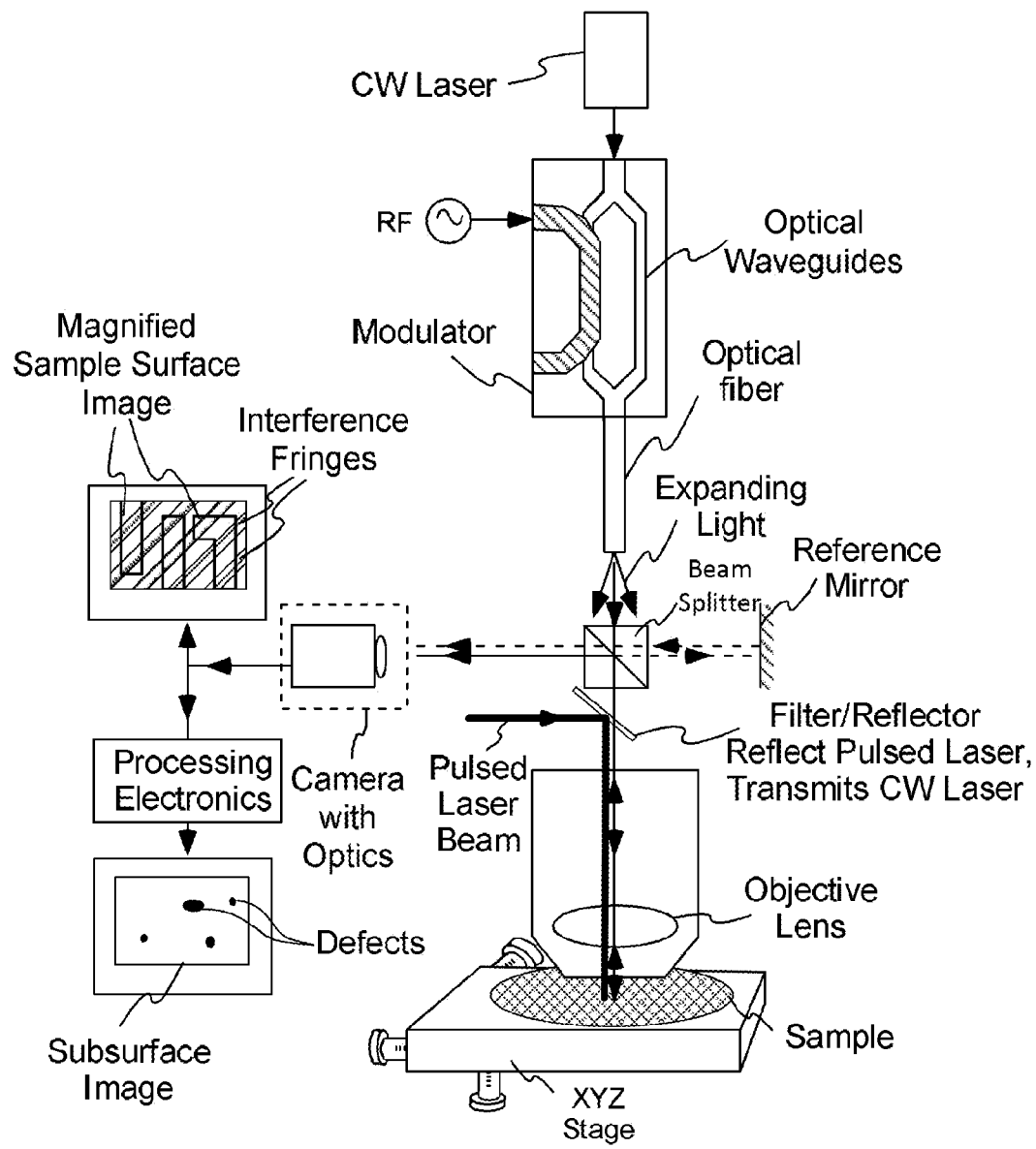
Figure 3C:
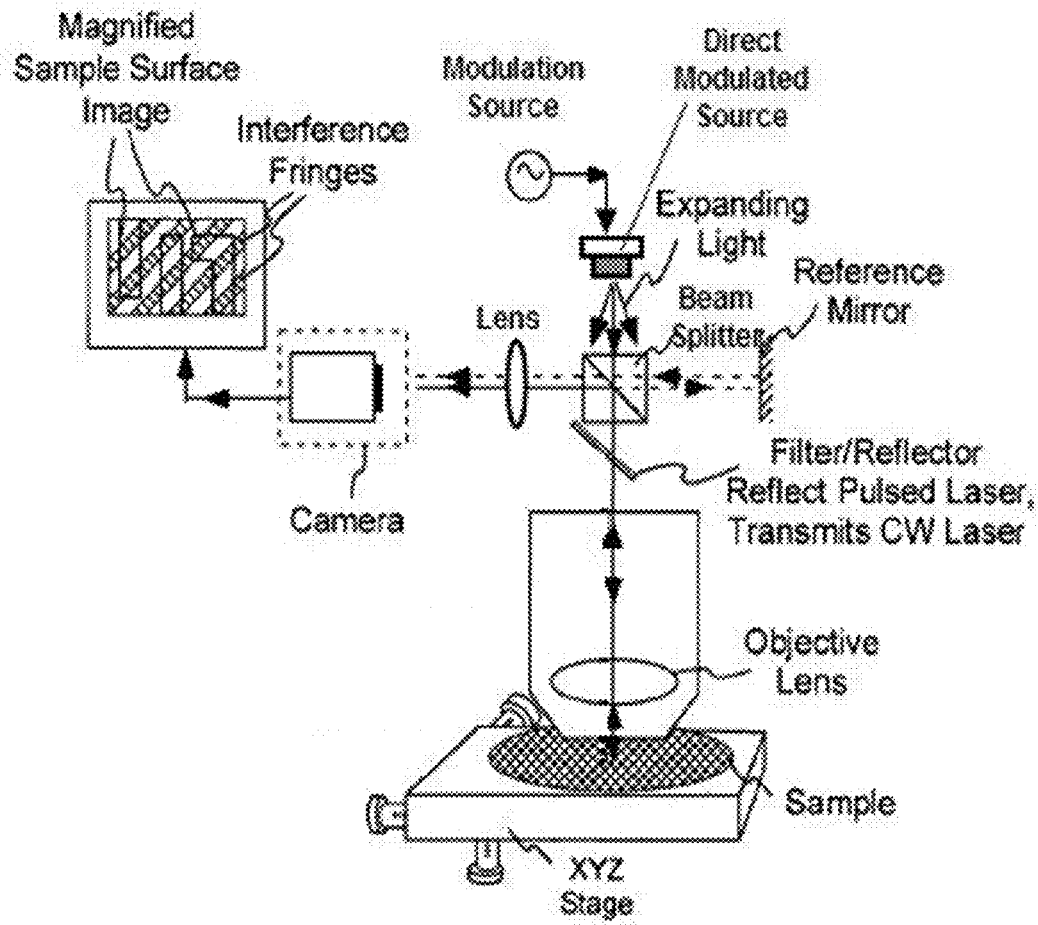

Referring to FIGS. 3A, 3B, and 3C, schematic block and pictorial diagrams show an interferometric microscope apparatus similar to what is described in Yacoubian (U.S. Pat. No. 7,397,596 B2), in which the output of the detector array is processed as described in FIG. 1 herein, yielding surface topography and subsurface images. In FIGS. 3A and 3B, the light source followed by an external modulator. In FIG. 3C, the light source is direct modulated.

Figure 4A:
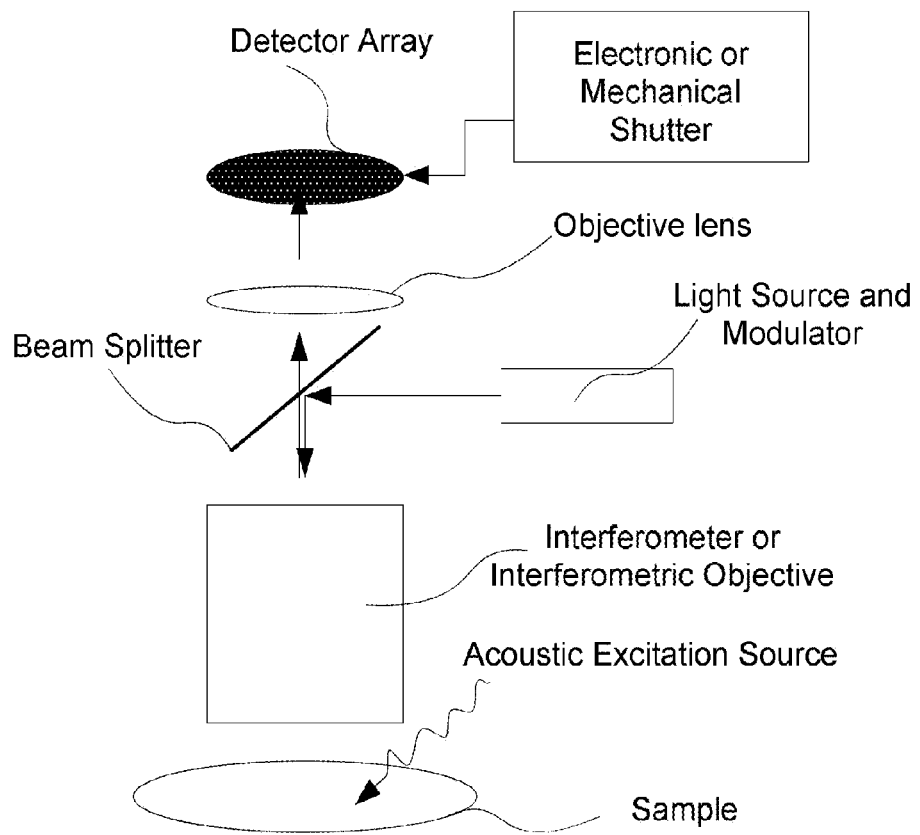
FIGS. 4A, 4B, and 4C are schematic block and pictorial diagrams depicting an apparatus that uses various types of interferometers, such as an interferometric objective-based microscope, a free space interferometer, or a waveguide-based interferometer, combined with an acoustic excitation source to yield surface and subsurface images.
Figure 4B:
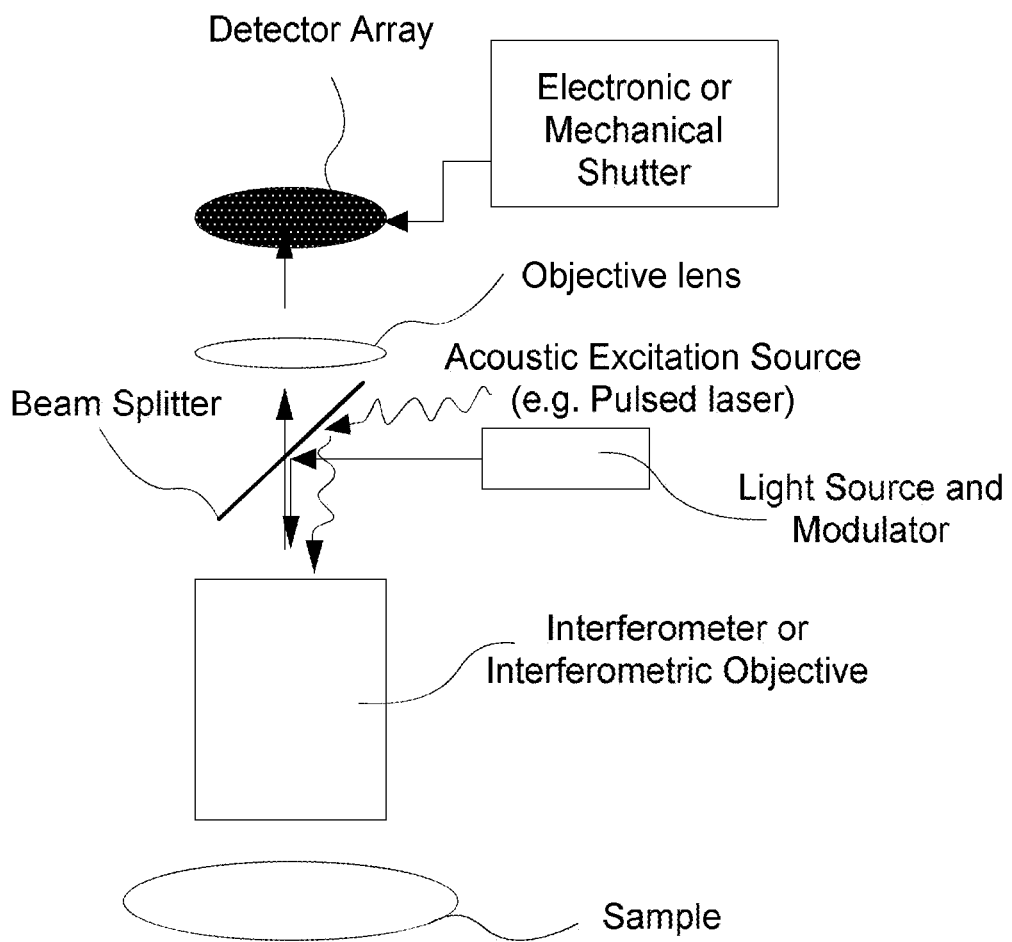
Figure 4C:
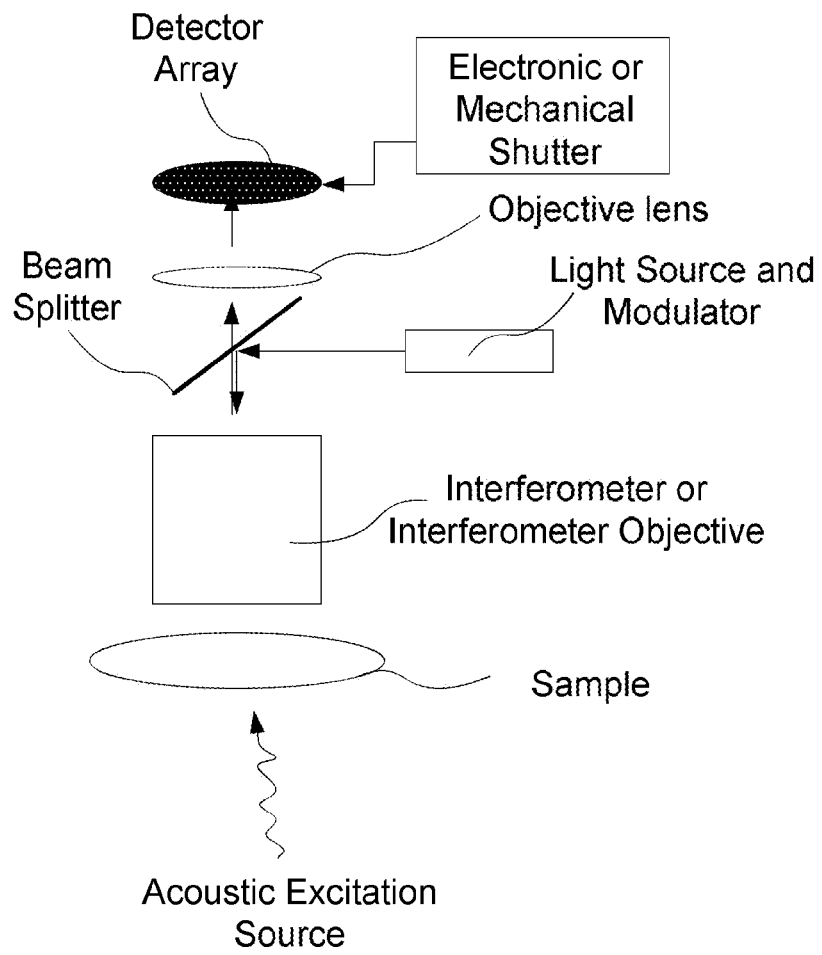

FIGS. 4A, 4B, and 4C are schematic block and pictorial diagrams depicting an apparatus that uses various types of interferometers, such as an interferometric objective-based microscope, a free space interferometer, or a waveguide-based interferometer, combined with an acoustic excitation source to yield surface and subsurface images. In addition, an optional electronic or mechanical shutter can be used in front of the detector array or camera. The shutter frequency and duty cycle can be optimized to match the desire difference frequency detection. In addition, the shutter modulation can be used for lock-in amplification. FIGS. 4A, 4B, and 4C show various examples of acoustic excitation methods by illuminating the sample with a pulsed laser. FIGS. 4A and 4B show front side illumination, and FIG. 4C illustrates back side illumination of the sample with a pulsed laser. The light source and modulator can be either a single modulator, or a direct modulated laser, while light, broadband, or superluminescence source.

Figure 5:
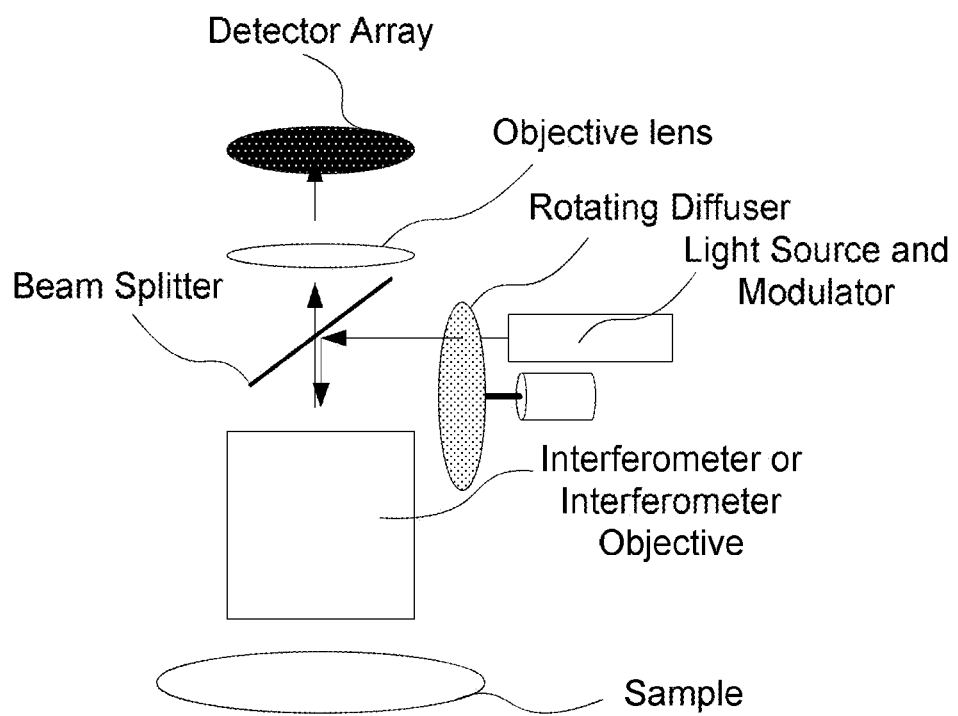
FIG. 5 is a schematic block and pictorial diagram showing use of a moving diffuser in the light path when the light source is a coherent or a partially coherent source.

Referring to FIG. 5, a schematic block and pictorial diagram showing use of a moving diffuser in the light path when the light source is a coherent or a partially coherent source. Using diffuser generates clear interference pattern while using a coherent source, such as a laser.

The apparatus described by Yacoubian (U.S. Pat. No. 7,397,596 B2) can produce image of the surface and the subsurface, including subsurface features and defects. High resolution topographic data can also be obtained from the apparatus. A suitable imaging technique can be performed as follows:

The subsurface features and defects can be detected by acoustically exciting the sample under test, and using detection scheme and apparatus described in Yacoubian (U.S. Pat. No. 7,397,596 B2) and Yacoubian (U.S. Pat. No. 7,463,364 B2).

The surface topography can be detected by introducing a phase shift between the reference and object beams of the interferometer shown throughout Yacoubian (U.S. Pat. No. 7,397,596 B2) and Yacoubian (U.S. Pat. No. 7,397,596 B2). Detection can be achieved in number of ways, such as by moving the reference mirror, by moving the object (i.e. the sample under test), by scanning an interferometric objective (such as when a Mirau Interferometeric objective is used), by introducing a phase element in the reference or object beam path, by polarization control of the reference or object beam, or any other means to cause phase shift and scan the interferomatric fringes, such as depicted in FIGS. 1A and 1B of Yacoubian (U.S. Pat. No. 7,397,596 B2) and throughout Yacoubian (U.S. Pat. No. 7,397,596 B2) and Yacoubian (U.S. Pat. No. 7,463,364 B2).

Surface topography can be obtained using a coherent light source and from fringe information as is done with standard interferometric microscopy. For example, the fringes will be shifted in response to a topography variation. Furthermore, precise topographic measurement can be made by using a coherent, partially coherent or incoherent light sources. Topographic measurements can be achieved in a number of ways, such as a) shifting the phase between the reference and object beams, b) using multiple light sources of different wavelengths, or c) using a white light (or broadband) light source, and d) scanning the sample or the objective lens.

When the surface topographic measurement is combined with the subsurface measurement technique described in Yacoubian (U.S. Pat. No. 7,397,596 B2) and Yacoubian (U.S. Pat. No. 7,463,364 B2), the resulting outcome is a topographic image of the surface as well as topographic image of the subsurface, and also indication of presence of defects, material variations, stress, surface and subsurface cracks, discontinuities, gaps, thickness variations, and other features in the subsurface.

An example of apparatus that can achieve surface and surface imaging with or without modification that are described herein are depicted by Yacoubian in FIGS. 1-4 and 25 of Yacoubian (U.S. Pat. No. 7,397,596 B2).

An apparatus that can achieve both surface and subsurface imaging as described hereinabove can utilize either a single light source, two or more different light sources, and a single or multiple detectors and detector arrays.

To avoid interfering between the surface metrology measurement and depth imaging and subsurface measurements, several methods and devices can be utilized, such as:

Usage of separate optical filters to filter out each wavelength from the light sources that are used for surface and subsurface imaging.

Using polarization optics to separate subsurface measurements and surface metrology.

Utilizing various light source modulation schemes with various modulation frequencies.

Using phase modulation schemes with various modulation frequencies.

In some embodiments, the various filtering techniques, optics, and or modulation techniques can be combined. In an illustrative combination of devices and techniques, electronic filtering (such as using analog or digital filters) such as low-pass, band pass or high pass filter, or a combination of several types of filters can be employed. Similarly, some embodiments can use software filtering, such as low-pass, band pass or high pass filter, or a combination of several types of filters. Other embodiments can use a combination of electronic and software filtering.

An example technique for use of the illustrative imaging apparatus for surface and subsurface can be described in the following manner. For a single imaging array, a set of interference fringes can be observed that contain both the surface and subsurface data. Assuming the subsurface data produced by the difference in modulator frequency and elastic wave modulation (as described in Yacoubian (U.S. Pat. No. 7,397,596 B2) and Yacoubian (U.S. Pat. No. 7,463,364 B2)) are due to acoustic excitation, then the fringes will be modulated at the difference frequency. Information can be obtained about the subsurface using an electronic or software filter that passes the difference frequency. Alternatively, the stationary portion of the fringes represents the surface topographic data.

Often an acoustic signature contains coupled surface and subsurface data. To distinguish between the surface and subsurface features, the following can be performed. First a surface topography can be measured using stationary fringes while the acoustic excitation source is turned off. Then the acoustic excitation source is activated and the data is captured by filtering out difference frequency modulated fringes. Next the true sub-surface information can be extracted by comparing the surface topography data and the data obtained during acoustic excitation using various signal and image processing techniques. Examples of signal and image processing techniques include correlation, convolution, signal or image subtraction, wavelet processing, or any number of image and signal processing techniques that are known to one of ordinary skill in the art.

VARIOUS EMBODIMENTS

In another embodiment, the subsurface sensing can be combined with a white light interferometer to produced surface topographic image and subsurface image or subsurface map of features and defects.

Referring to FIGS. 1-4 and 25, and other figures throughout Yacoubian (U.S. Pat. No. 7,397,596 B2), the detection light source can be a single or multiple light sources, such as a laser, a white light source, a light emitting diode, or incoherent light source. The light source or multiple light sources can be combined with various types of optical filters to select an optical spectrum, such as colored filters, interference filters, polarization filter, spatially varying optical filters, or a combination of one or more of types of optical filters.

To achieve modulation for the subsurface imaging, an external modulator may be utilized, such as an electro-optic modulator, a liquid crystal light modulator, acousto-optic modulator, or any external modulated device. In another embodiment, the light source can be a direct modulation light source.

The modulated light can be primarily used for subsurface detection. However the surface detection can also utilize a modulated light source of different frequency, and selective frequency filtering at multiple frequencies can be utilized to distinguish between the surface topography and subsurface data as described herein.

In another embodiment, the light source can be a single light source used both for surface and subsurface detection, and can be modulated either two or more different frequencies, one for subsurface detection (e.g. using high frequency modulation), and the other for surface metrology. Alternatively, a single light source can be modulated using a single high-frequency for subsurface detection which, for surface metrology the signal can be low-pass filtered, using either the average signal, or a DC biased light source containing both DC and AC modulation.

In other embodiments, to produce interference fringes as depicted in FIGS. 1-4 and 25, and other figures throughout Yacoubian (U.S. Pat. No. 7,397,596 B2), the light source can be a white light source, a light emitting diode, an incoherent light source, a laser or a laser diode, or the like.

In other embodiments, the interferometric apparatus similar to those depicted in FIGS. 1-4 and 25, and other figures throughout Yacoubian (U.S. Pat. No. 7,397,596 B2), the beam splitter and the objective lens may be combined into a single unit, such as an interferometric objective lens or a Mirau Interferometer or a Mirau interferometric objective.

In other embodiments, the beam splitter (for example beam splitter 118 of FIG. 1B of Yacoubian (U.S. Pat. No. 7,397,596 B2), or beam splitter 218 of FIGS. 2A and 2B of Yacoubian (U.S. Pat. No. 7,397,596 B2)) can be placed in front of the objective using a Michelson interferometer configuration, which is generally suitable for low magnification (e.g. less than 5×) objectives, or with long working distance objective lenses.

In other embodiments, the beam splitter (for example beam splitter 118 of FIG. 1B of Yacoubian (U.S. Pat. No. 7,397,596 B2), or beam splitter 218 of FIGS. 2A and 2B of Yacoubian (U.S. Pat. No. 7,397,596 B2)) can be placed between two objective lenses to achieve straight fringes in a configuration similar to a Linnik interferometer. The two objectives can be the same optical power, or can be different lenses or lens systems. If different, fringes generated by the interferometer will not be linear, which can be corrected in several ways, such as by placing a refractive or diffractive optical element between the reference beam objective and the reference mirror, or by using a curved reference mirror placed in a manner that the phase fronts of the reference and object beams match, and therefore generate linear fringes. In other embodiments, the reference beam may not contain an objective lens, instead using a curved mirror to produce straight fringes.

In other embodiments, the beam splitter (for example beam splitter 118 of FIG. 1B of Yacoubian (U.S. Pat. No. 7,397,596 B2), or beam splitter 218 of FIGS. 2A and 2B of Yacoubian (U.S. Pat. No. 7,397,596 B2)) can be placed in front of the objective instead of behind, specifically between the objective lens and the sample under test. Either a beam splitter that is used to split the reference and object beams, or a beam splitter to separate two sources, one for surface detection and another for subsurface acoustic excitation, can be placed in such configuration. In another embodiment, the function of the reference/object beam splitter and a beam splitter to separate the acoustic excitation source can be combined using either a dichroic mirror or a multi-layer wavelength selecting beam splitter, a polarization beam splitter, a spatially selective transmission optical beam splitter, or any other combination. To avoid saturation of the detector array, the acoustic excitation source should be filtered out using various filtering schemes as described herein, by physically separating the two light beams (as shown in FIG. 1B of Yacoubian (U.S. Pat. No. 7,397,596 B2)), and by using wavelength selective optical filters in front of the detector array.

In another embodiment, the three-dimensional surface metrology can be generated using a two-dimensional (2D) imaging sensor array, while a single pixel subsurface detection can be achieved by acoustically exciting the sample at a single point, and detecting the signal containing the subsurface information using either the imaging sensor array that is used for surface metrology combined with the appropriate electrical or software filtering described hereinabove, or using a single point detector.

In another embodiment, the three-dimensional surface metrology can be generated using a two-dimensional (2D) imaging sensor array, while a line scanned subsurface detection can be achieved by acoustically exciting the sample using a line source utilizing a cylindrical refractive, diffractive or reflection optical element (see for example FIG. 4B of Yacoubian (U.S. Pat. No. 7,397,596 B2)), by a scanning beam apparatus (e.g. a scanning mirror), and detecting the signal containing the subsurface information using either the imaging sensor array that is used for surface metrology combined with the appropriate electrical or software filtering as described hereinabove, or using a separate single point detector, a linear array or a 2D detector array.

In another embodiment, the three-dimensional surface metrology can be a generated using a two-dimensional (2D) imaging sensor array, while a x-y scanned subsurface detection can be achieved by acoustically exciting the sample using a scanning line source utilizing a cylindrical refractive, diffractive or reflection optical element (see for example FIG. 4B of Yacoubian (U.S. Pat. No. 7,397,596 B2)), and by scanning the line scan in one dimension e.g. using a scanning mirror.

In another embodiment, the three-dimensional surface metrology can be a generated using a two-dimensional (2D) imaging sensor array, while a x-y scanned subsurface detection can be achieved by acoustically exciting the sample using a single point excitation, and x-y scanning using a scanning mirror.

In another embodiment, x-scanned or a x-y scanned subsurface image can be generated by scanning the sample in one dimension, while utilizing a single point subsurface detection scheme as described hereinabove.

In another embodiment, x-y scanned subsurface image can be generated by scanning the sample in two dimensions while using a single point subsurface detection scheme as described hereinabove.

Yet in another embodiment, x-y scanned subsurface image can be generated by scanning the sample in one-dimensions while using a line-scanned subsurface detection scheme as described hereinabove.

In another embodiment, the light source can be frequency modulated, causing shifting of the fringes, which can be used for subsurface detection using the beat frequency detection approach described in Yacoubian (U.S. Pat. No. 7,397,596 B2), or for surface metrology, which uses shifting of the fringes to calculate the surface topography. The same source can be modulated at two or more different frequencies and the detected fringe pattern can be electrically or software filtered to distinguish between the surface and subsurface measurements.

In other embodiments, the pulsed laser that is used for generating elastic waves for subsurface imaging can be replaced or combined with by one or more of the following: (1) an acoustic transducer, (2) an acoustic transducer such as a piezoelectric transducer, (3) an acoustic transducer air coupled to the sample, (4) an acoustic transducer liquid coupled to the sample, (5) a surface acoustic wave generator, (6) a surface acoustic wave generator either coupled to the sample (e.g. fluid coupling), or is part of the sample itself, or the sample holder or substrate, (7) a thermal source, (8) a pulsed thermal source, (9) an electro-magnetic source, (10) an electro-magnetic source, such as an RF source, (11) a terahertz (THz) source, (12) a pulsed electro-magnetic source, (13) a pulsed light source, (14) a modulated light source, or the like.

In another embodiment, the apparatus can be used to detect resonance structures, such as a membrane structure or a micro-electro-mechanical (MEMS) sample. When a resonant structure is used as a sample, the resonance frequencies can be generated either using an external source as described herein throughout and in Yacoubian (U.S. Pat. No. 7,397,596 B2) and Yacoubian (U.S. Pat. No. 7,463,364 B2), or by using the test sample's internal excitation. For example, a MEMS sample resonance can also be excited by applying electrical modulation directly to the sensor electrodes. Testing the resonant characteristics of the sample, and measuring any deviation from expected resonance frequencies indicates potential problems and defects that are not easily detected using surface topography. Examples of resonance detection are described in Yacoubian (U.S. Pat. No. 7,397,596 B2) and Yacoubian (U.S. Pat. No. 7,463,364 B2).

Obtaining Smooth Images Using Coherent Source

In various embodiments, an optical imager may implement a suitable speckle reduction method. Similar methods for obtaining high-resolution surface images are described by Yacoubian (U.S. patent application Ser. No. 11/733,540).

Figure 6B:
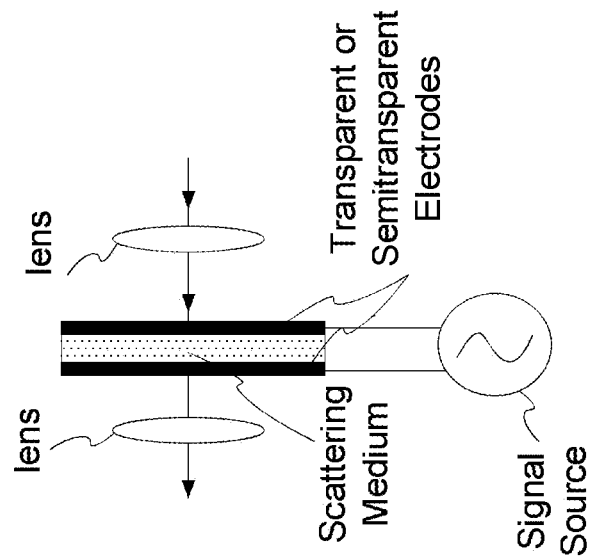
Figure 6A:
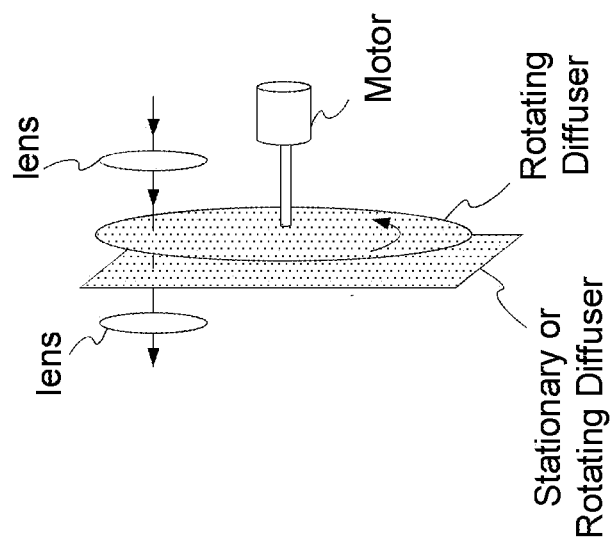

Referring to FIGS. 6A, 6B, 6C, 6D, and 6E, schematic pictorial diagrams show variations of an apparatus that uses a moving diffuser in the light path when the light source is a coherent or a partially coherent source as shown in FIG. 5 in a manner that reduces or minimizes the effect of speckle pattern when a coherent source is used. If a coherent source such as a laser is used as the input light source to the high-resolution imaging schemes described in several places herein, the interference pattern can contain a speckle. The speckle pattern can be a source of noise. To reduce or eliminate the speckle noise, yet still be able to use a highly coherent source, various speckle reduction methods can be used. One method involves passing light through a moving random media, such as a rotating diffuser as depicted in FIG. 6A, a linearly moving diffuser as shown in FIG. 6D, a moving random media such as a liquid crystal type material mixed with a scattering medium as seen in FIG. 6B, or a flowing scattering medium circulated with a pump as in FIG. 6C. Using a suitable technique, speckle can be reduced by moving the random media such that speckles move at higher rate than the camera image capture speed, and the interference pattern is smoothed. A randomizing apparatus can generally be placed at the input terminal of the interferometer but may also be placed in any suitable position throughout the optical path of the optical system. When used at the input terminal of the optical system, at least two lenses or equivalent optical components, one before the random media and one after, may be desired. One lens can control the spot size of the light incident on the random media, thus controlling the speckle sizes, and can control the desired image smoothness without losing the interference pattern.

An optical imager can include a speckle reduction device configured for usage with a coherent source including first and second lenses configured to receive and pass illumination from the coherent source, a rotating diffuser positioned between the first and second lenses, and a rotating motor. The rotating motor is operative to rotate the rotating diffuser whereby a captured image is a time average of moving speckle patterns, an interference image is smoothed, and speckle noise is reduced or eliminated. Referring to FIG. 6A, a schematic pictorial and block diagram illustrates an embodiment of a spectral reduction device and associated speckle reduction method using a rotating diffuser via a rotating motor when using a coherent source as the light source to the high-resolution imaging apparatus described herein throughout. When the diffuser rotates, the speckle pattern generated by the coherent source also moves. When the speckles move much faster than the image capture rate of the camera, the captured image is a time-averaged image of the moving speckle patterns, thus the interference image is smoothed and speckle noise is greatly reduces or eliminated. The spatial coherence is directly proportional to the speckle size. To control the speckle size, a lens is used to adjust the spot size incident on the rotating diffuser, thus controlling the spatial coherence of light. An optional stationary diffuser may be placed after the moving diffuser such that speckle movement is in random orientation rather than in directional of the diffuser movement.

In other examples, an optical imager can include a speckle reduction device configured for usage with a coherent source including first and second lenses configured to receive and pass illumination from the coherent source, and an electrically-motile scattering medium embedded between two transparent or semitransparent electrodes positioned between the first and second lenses whereby a captured image is a time average of speckle patterns moved by application of voltage across the electrodes, an interference image is smoothed, and speckle noise is reduced or eliminated. Referring to FIG. 6B, a schematic pictorial and block diagram depicts an embodiment of a spectral reduction device and associated speckle reduction method using a scattering medium embedded between two transparent or semitransparent electrodes when using a coherent source as the light source to the high-resolution imaging apparatus described herein in various places. The medium can be a liquid crystal type material mixed with a scattering medium, or any type of medium that can be moved electrically. By applying a voltage across the electrodes, the random medium is moved, thus moving the speckles generated by the coherent source. The interference images captured by the apparatus discussed herein throughout contain speckle noise if a highly coherent light source is used. When the speckles move much faster than the image capture rate of the camera, the captured image is a time averaged image of the moving speckle patterns, thus the interference image is smoothed and speckle noise is greatly reduces or eliminated. The spatial coherence is directly proportional to the speckle size. To control the speckle size, a lens is used to adjust the spot size incident on the random medium, thus controlling the spatial coherence of light.

In still other configurations, an optical imager can include a speckle reduction device configured for usage with a coherent source including first and second lenses configured to receive and pass illumination from the coherent source, a liquid pump, and a scattering medium circulated by the liquid pump. In the arrangement a captured image is a time average of moving speckle patterns, an interference image is smoothed, and speckle noise is reduced or eliminated. Referring to FIG. 6C, a schematic pictorial and block diagram illustrates an embodiment of a spectral reduction device and associated speckle reduction method using a flowing scattering medium when using a coherent source as the light source to the high-resolution imaging apparatus described herein throughout. The scattering liquid medium is circulated by a liquid pump, thus moving the scattering medium. Light from the source is incident on an optical window filled with the flowing scattering media, and speckles generated by the coherent source move due to the movement of the scattering medium. When the speckles move much faster than the image capture rate of the camera, the captured image is a time averaged image of the moving speckle patterns, thus the interference image is smoothed and speckle noise is greatly reduces or eliminated. To control the speckle size, a lens is used to adjust the spot size incident on the random medium, thus controlling the spatial coherence of light.

In further arrangements, an optical imager can include a speckle reduction device configured for usage with a coherent source including first and second lenses configured to receive and pass illumination from the coherent source, a motion device, and a scattering medium moved by the motion device whereby a captured image is a time average of moving speckle patterns, an interference image is smoothed, and speckle noise is reduced or eliminated. In various embodiments, the motion device can be a translation stage, a motorized stage, a solenoid-based moving apparatus, a piezoelectric moving stage, and a linear translation driver. Referring to FIG. 6D, a schematic pictorial and block diagram illustrates an embodiment of a spectral reduction device and associated speckle reduction method using a linearly moving diffuser with a coherent source as the light source to the high-resolution imaging apparatus described herein throughout. Movement is achieved using moving apparatus such as a translation stage, a motorized stage, a solenoid based moving apparatus such as an audio speaker, a piezoelectric moving stage, or any other means of producing a linear translation. The moving apparatus is translated linearly back and forth, thus producing movement of the speckle pattern generated by the coherent source. The moving apparatus is either controlled by an electrical source or by the control electronics. When the speckles move much faster than the image capture rate of the camera, the captured image is a time averaged image of the moving speckle patterns, thus the interference image is smoothed and speckle noise is greatly reduces or eliminated. The spatial coherence is directly proportional to the speckle size. To control the speckle size, a lens is used to adjust the spot size incident on the rotating diffuser, thus controlling the spatial coherence of light. An optional stationary diffuser may be placed after the moving diffuser such that speckle movement is in random orientation rather than in the direction of the diffuser movement.

Figure 6E:
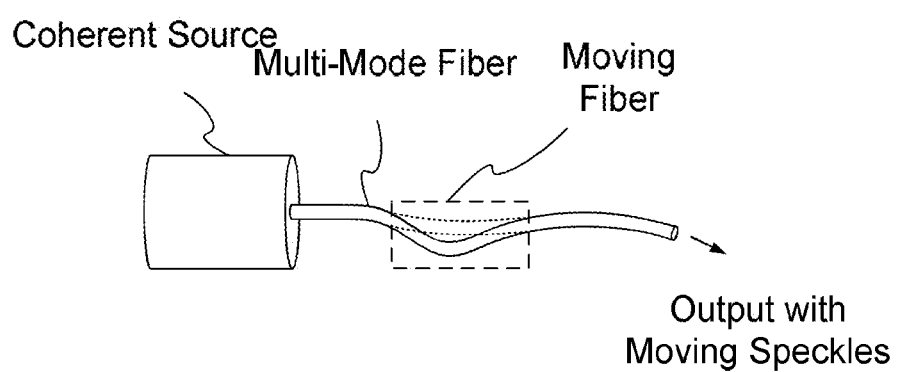

In further arrangements, the interferometric instrument can include a speckle reduction device configured for usage with a coherent source comprising of a coherent source, such as a laser or a laser diode, a multimode fiber, and a motion device that moves, bends, vibrates or stretches the multimode fiber, as depicted in FIG. 6E. Examples of the motion device can be a motor driven mechanism, a piezoelectric to the fiber, or the fiber wound around a cylindrical piezoelectric element. The motion of the multimode fiber causes the speckle of the interference image to move. While inducing the motion of the fiber, the interference image is captured and the image is averaged either by way of electronics, such as low pass filtering, or by way of the speckle movement being faster than the image capture rate of the camera, or using a software averaging of digitally captured image, or a combination thereof. Referring to FIG. 6E, a schematic pictorial and block diagram illustrates an embodiment of a spectral reduction device and associated speckle reduction method using moving multimode fiber. In various embodiments, the motion device can be a translation stage, a motorized stage, a solenoid-based moving apparatus, a piezoelectric moving stage, and a linear translation driver. The moving apparatus is either controlled by an electrical source or by the control electronics. When the speckles move much faster than the image capture rate of the camera, the captured image is a time averaged image of the moving speckle patterns, thus the interference image is smoothed and speckle noise is greatly reduces or eliminated.

Figure 6F:
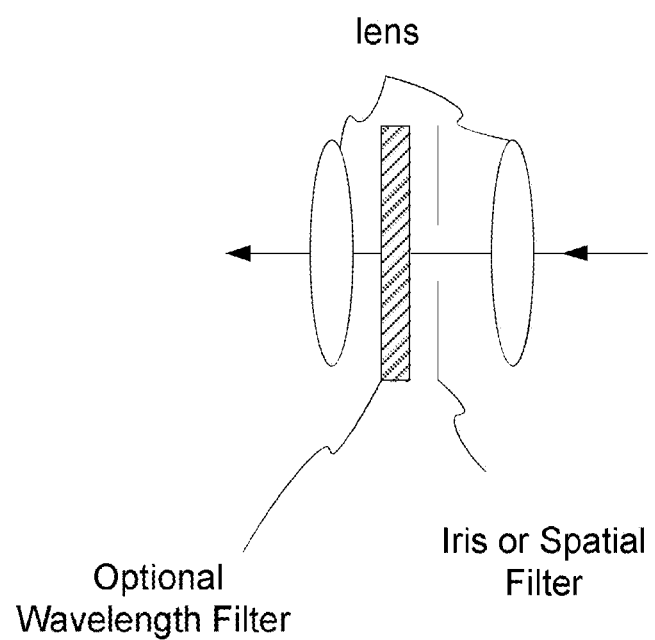

Referring to FIG. 6F, an apparatus is shown which may be used in front of the source/modulator where a low-coherence source is used to minimize speckle noise, and is combined with a spatial filter, an optical wavelength filter, or any combination thereof, to increase the coherence length. Another approach to reduce speckles is to use a low-coherence optical source, such a light emitting diode (LED), a halogen light, or any available low-coherence light source, as depicted in FIG. 6F. Additionally, an iris or a spatial filter may be inserted between the lenses to filter out intensity variations of the source. An optional wavelength filter may be used to tune a wide-band optical source to a desirable narrow-band wavelength range.

As shown in FIG. 6F, the embodiment of a spectral reduction device and associated speckle reduction method can use a partially coherent light source, such as a halogen lamp, a thermal lamp of any suitable type, light emitting diode, super luminescence source, or a low coherence laser. Lenses or a combination of lenses can be used to control the light divergence/convergence or collimation. An optional iris or a spatial filter may be inserted between the lenses to filter out intensity variations of the source. An optional wavelength filter may be used to tune a wide-band optical source to a desirable narrow-band wavelength range.

Increase Coherence Length

In another embodiment, such as depicted in FIG. 6F a low-coherence source can be used to minimize speckle noise, and is combined with a spatial filter, an optical wavelength filter, or any combination thereof, to increase the coherence length. Increasing the coherence length will result in less stringent requirements to match the object and reference beams of the interferometer.

Optimizing Signal Detection

In another embodiment, the shutter control shown in FIG. 4 can be optimized to match the desired difference frequency and the shutter modulation, where the difference frequency is the frequency between the acoustic excitation frequency and detected signal modulation, as described in Yacoubian (U.S. Pat. No. 7,397,596 B2) and Yacoubian (U.S. Pat. No. 7,463,364 B2).

In another embodiment, additional modulation can be added either to the acoustic excitation source, to the modulated light source, or both, and the signal can be used in a lock-in configuration to minimize signal to noise ratio. In addition, the camera shutter control can also be used in this lock-in configuration. Lock-in detection can be used to minimize noise and detected signal even if the signal is buried in noise.

Various Detection Signals

The apparatus depicted in various places herein can detect surface and subsurface features and defects utilizing variation detection mechanisms. Suitable techniques can include detection of surface vibration, subsurface vibration, vibration at the back of the sample, detection of real or complex refractive index variation near the surface or inside the sample under test, or absorption change near the surface or inside the sample under test, and the like.

Polarization Interferometer and Phase Shifted Fringe Images

In another embodiment that is similar to the systems and devices shown in FIGS. 2A, 2B, 2C, 3A, 3B, and 3C, the interferometer can be a polarization interferometer, where the beam splitter is replaced by a polarization beam splitter, to produce interference fringes from light reflected from the surface of the sensor.

In another embodiment similar to the systems and devices shown in FIGS. 4A, 4B, 4C, and 5, the interferometric objective can be replaced with a polarization sensitive interferometric objective, and additional polarization sensitive components can be used to produce interference fringes from light reflected from the surface of the sensor.

In another embodiment that is similar to the systems and devices shown in FIGS. 2A, 2B, 2C, 3A, 3B, 3C, 4A, 4B, 4C, and 5, the beam splitter or the interferometric objective can be replaced by polarization beam splitter or polarization interferometric objective, and additional polarization sensitive components such as polarizers and retarders can be used in the beam path to produce interference fringes.

In another embodiment that is similar to the systems and devices shown in FIGS. 2A, 2B, 2C, 3A, 3B, 3C, 4A, 4B, 4C, and 5, the detector array can be a polarization sensitive detector array, fabricated by having a filter array in front of the photo-detector, monolithically integrated with the detector array, or using multiple cameras with polarization sensitive beam splitters to produce multiple phase sensitive measurement. Individual images produce a separate phase shifted interference fringe with respect to the other images. The fringe images can be processed, for example by detecting the difference or the relative position of the fringes, reducing vibration noise since the separate image shifts in the same relative direction when the apparatus moves.

In another embodiment that is similar to the systems and devices shown in FIGS. 2A, 2B, 2C, 3A, 3B, 3C, 4A, 4B, 4C, and 5, a component such as a holographic component, a computer generated hologram, or polarization sensitive component, can be placed in the beam path in front of the camera to produce multiple images, the individual images produce phase shifted interference fringes with respect to the other images. The fringe images can be processed, for example by determining the difference of the relative position of the fringes, thereby reducing vibration noise since the separate image shifts in the same relative direction when the apparatus moves.

Example Applications of Surface and Subsurface Inspection

The surface and subsurface inspection technology described herein can be used in a variety of applications in which a non-contact, non-destructive tool is used for inspection. Some applications include: (1) inspection of semiconductor wafers (processed or during each processing step) for subsurface defects, and for accuracy of subsurface; (2) detecting micro-cracks and micro-defects in solids; (3) detecting subsurface features hidden under layers that are optically opaque, or the like.

The tools capability for inspecting both surface and subsurface features, enables usage for comparing and correlating surface and subsurface features and defects, and determination of a root cause of a defect that may be caused by a surface feature.

Figure 7:
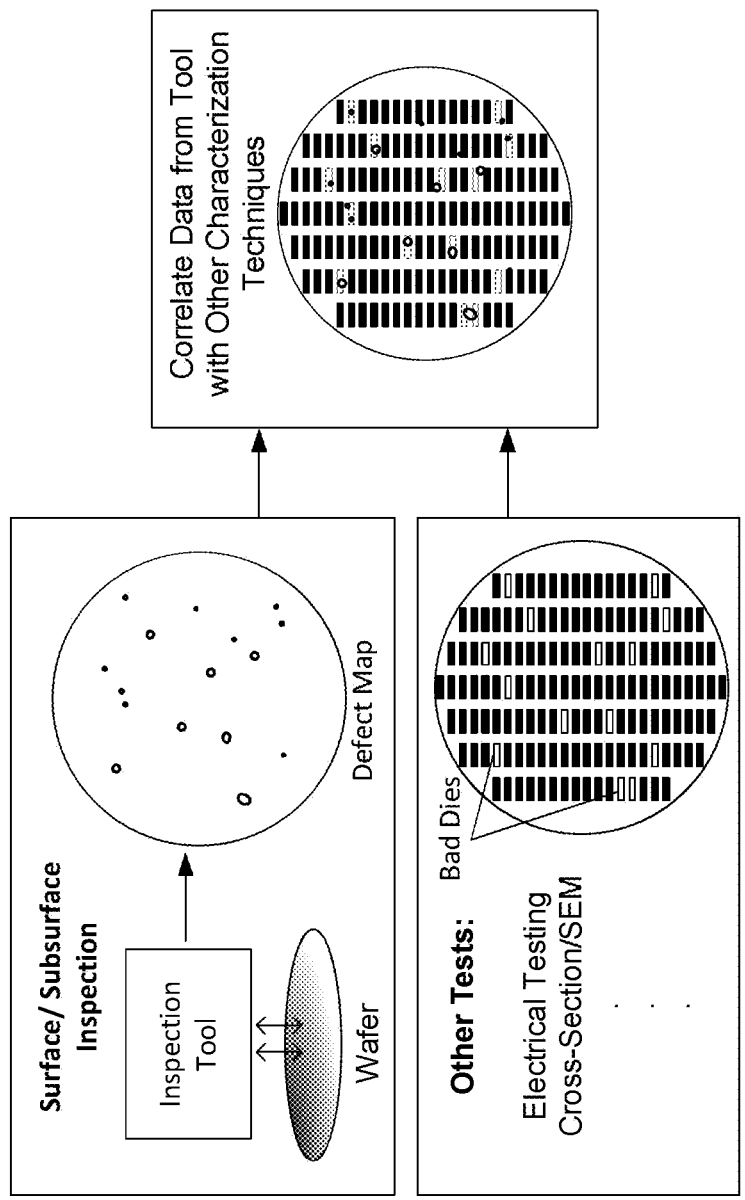
FIG. 7 is a schematic block and pictorial diagram illustrating comparison of a surface/subsurface defect map with test results of the final integrated circuit obtained by other means, such as electrical testing or cross-sectioning.

Referring to FIG. 7, a schematic block and pictorial diagram illustrates operations for comparing surface/subsurface defect map with test results of the final integrated circuit obtained by other means, such as electrical testing or cross-sectioning. The defect map produced by the characterization techniques described in various places herein can be used by a wafer manufacturer, correlated with the defective die or pixel map of the processed wafer. Corrective action can be taken to optimize the wafer processing parameters to minimize defects, to maximize yield, or to maximize pixel operability, or the like.

Another application can be usage of the tool to inspect semiconductor wafers in between processing steps to detect surface and subsurface defects, and comparing the findings with the final processed wafer that is tested by other techniques, such as electrical testing or testing using a cross-section, as depicted in FIG. 7. The correlated data can yield the root cause of the failure.

Yet in another application, the tool can be used to inspect a fully patterned and functional semiconductor integrated circuit (IC) non-destructively, to find defects in the IC that can cause failure.

Examples of types of subsurface defect and features that can be detected are voids, inclusions, delamination, variations in material density, micro-cracks. In addition, the shape and dimensions of a subsurface features and layers can be determined. The subsurface structure, including shape, location and dimensions affects the elastic wave propagation and can result in a different frequency response. Therefore scanning the frequency (e.g. varying the modulation frequency depicted in FIGS. 3A, 3B, 3C, 4A, 4B, and 4C) yields information about the subsurface structure.

Other examples of suitable applications of the technology can include detection of features and defects in semiconductor, metallic and dielectric materials, in electronic circuits, and semiconductor detector materials, and wafers used for electronic circuits.

An additional example application can be detection of defects such as dislocations, inclusions, or precipitates in focal plane arrays (FPA) used at various stages of processing of the FPA wafer.

Another example application can be performance of failure analysis for semiconductor integrated circuits by finding subsurface defects, or to find dimensional deviation from the design specifications, to find the root cause of the failure.

Yet another example application can be screening for voids between contacts in three dimensional stacked wafers.

In the illustrative embodiments, surface and subsurface imaging can be performed using subsurface imaging by acoustical excitation and optical detection, and interferometric surface topographic measurement.

In some embodiments, surface and subsurface imaging can be performed using white light interferometer combined with acoustic excitation source. Various types of interferometer light source can include broadband sources, incoherent sources, partially coherent light sources, an externally modulated source, a direct modulated source, or the like.

Similarly, various embodiments can include one or more acoustic excitation sources including, for example, (1) lasers, (2) pulsed lasers, (3) modulated lasers, (4) coherent, incoherent or partially coherent light sources, (5) a pulsed light source, (6) a modulated light source, (7) an acoustic transducer, (8) an acoustic transducer such as a piezoelectric transducer, (9) an acoustic transducer air coupled to the sample, (10) an acoustic transducer liquid coupled to the sample, (11) a surface acoustic wave generator, (12) a surface acoustic wave generator either coupled to the sample (e.g. fluid coupling), or is part of the sample itself, or the sample holder or substrate, (13) a thermal source, (14) a pulsed thermal source, (15) an electro-magnetic source, (16) an electro-magnetic source, such as an RF source, (17) a terahertz (THz) source, (18) a pulsed electro-magnetic source, or the like.

In various applications of the one or more embodiments, the sensor can perform detection of defects in electronic, semiconductor and metallic surface, electronic circuits, and detector materials, and wafers used for electronic circuits, detector materials, and focal plane arrays, or the like.

In some embodiment, the sensor can use information with feedback and testing to determine a source of defects, and to make correction for the defects.

In some embodiment, the sensor can use direct modulated source for acoustic excitation.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims.

What is claimed is:

1. A sensor comprising:
   a plurality of imaging components for imaging a sample configured to perform (1) subsurface imaging by acoustical excitation and optical detection, and (2) interferometric surface topographic measurement, wherein the plurality of imaging components further comprises:
   an image detector array;
   an acoustic excitation source configured to acoustically excite the sample to provide image information of a plurality of points of the sample;
   wherein the acoustic excitation source is a pulsed laser that propagates through free space;
   a stationary interferometric microscope configured to receive image information of the plurality of points of the sample from the image detector array; and
   a filter configured to separate the image information of the plurality of points of the sample into a surface component and a subsurface component.

2. The sensor according to claim 1 further comprising:
   a white light interferometer; and
   an interferometer light source including at least one of a broadband source, an incoherent source, a partially coherent source, an externally modulated source, and a direct modulated source.

3. The sensor according to claim 1 further comprising:
   at least one of
   an interferometer objective; or
   one or more polarization components.

4. The sensor according to claim 1 further comprising:
   an acoustic excitation source including at least one of a laser, a pulsed laser, a modulated laser, a coherent light source, an incoherent light source, a partially coherent light source, a pulsed light source, a modulated light source, a direct modulated source, an acoustic transducer, a piezoelectric acoustic transducer, an acoustic transducer air-coupled to a sample, an acoustic transducer liquid-coupled to the sample, a surface acoustic wave (SAW) generator, a surface acoustic wave (SAW) generator fluid-coupled to the sample, a surface acoustic wave (SAW) generator as at least part of the sample, a surface acoustic wave (SAW) generator configured as a sample holder, a surface acoustic wave (SAW) generator configured as a substrate, a thermal source, a pulsed thermal source, an electro-magnetic source, a radio frequency (RF) source, a terahertz (THz) source, or a pulsed electro-magnetic source.

5. The sensor according to claim 1 further comprising:
   the plurality of imaging components configured to perform detection of detects in at least one of (1) an electronic surface, (2) a semiconductor surface, (3) a metallic surface, (4) a combination of at least two of an electronic surface, a semiconductor surface, and a metallic surface, (5) an electronic circuit, (6) one or more detector materials, (7) one or more wafers used for electronic circuits, or (8) focal plane arrays.

6. The sensor according to claim 1 further comprising:
   a feedback loop configured to determine a source of defects in at least one of subsurface or surface images; and
   logic configured to correct for the defects in at least one of subsurface or surface images.

7. The sensor according to claim 1 further comprising:
   a speckle reduction device configured for usage with a coherent source including:
   first and second lenses configured to receive and pass illumination from the coherent source;
   a rotating diffuser positioned between the first and second lenses; and
   a rotating motor configured to rotate the rotating diffuser wherein a captured image is a time average of moving speckle patterns, an interference image is smoothed, and speckle noise is reduced or eliminated.

8. The sensor according to claim 1 further comprising:
   a speckle reduction device configured for usage with a coherent source including:
   first and second lenses configured to receive and pass illumination from the coherent source; and
   an electrically-motile scattering medium embedded between two transparent or semitransparent electrodes positioned between the first and second lenses wherein a captured image is a time average of speckle patterns moved by application of voltage across the electrodes, an interference image is smoothed, and speckle noise is reduced or eliminated.

9. The sensor according to claim 1 further comprising:
   a speckle reduction device configured for usage with a coherent source including:
   first and second lenses configured to receive and pass illumination from the coherent source;
   a liquid pump; and
   a scattering medium circulated by the liquid pump.

10. The sensor according to claim 1 further comprising:
a speckle reduction device configured for usage with a coherent source including:
   first and second lenses configured to receive and pass illumination from the coherent source;
   a motion device; and
   a scattering medium configured for movement via the motion device wherein a captured image is a time average of moving speckle patterns, an interference image is smoothed, and speckle noise is reduced or eliminated.

11. The sensor according to claim 10 wherein:
the motion device includes at least one of a translation stage, a motorized stage, a solenoid-based moving apparatus, a piezoelectric moving stage, and a linear translation driver.

12. The sensor according to claim 1 wherein the plurality of imaging components further comprises:
at least one of the acoustic excitation source or a modulated light source; and
a modulator configured to add modulation to the at least one of the acoustic excitation source or the modulated light source, the modulator configured for producing a signal for usage in a lock-in configuration to reduce signal-to-noise ratio.

13. An imaging method comprising:
providing a plurality of imaging components for imaging a sample configured to perform (1) subsurface imaging by acoustical excitation and optical detection, and (2) interferometric surface topographic measurement, the plurality of imaging components including at least
   an image detector array;
   an acoustic excitation source configured to acoustically excite the sample to provide image information of a plurality of points of the sample;
   wherein the acoustic excitation source is a pulsed laser that propagates through free space;
   a stationary interferometric microscope configured to receive image information of the plurality of points of the sample from the image detector array; and
   a filter configured to separate the image information of the plurality of points of the sample into a surface component and a subsurface component;
performing the subsurface imaging by acoustical excitation and optical detection; and
performing the interferometric surface topographic measurement.

14. The method according to claim 13 further comprising:
receiving image information from the image detector array;
acoustically exciting the sample to provide image information of the plurality of points of the sample by using the acoustic excitation source; and
using the filter to separate the image information of the plurality of points of the sample into a surface component and a subsurface component.

15. The method according to claim 13 further comprising:
acoustically exciting the image information of the plurality of points of the sample using a white light interferometer and an interferometer light source including at least one of a broadband source, an incoherent source, a partially coherent source, an externally modulated source, and a direct modulated source.

16. The method according to claim 13 further comprising:
acoustically exciting the sample to provide image information of the plurality of points of the sample by using the acoustic excitation source including at least one of a laser, a pulsed laser, a modulated laser, a coherent light source, an incoherent light source, a partially coherent light source, a pulsed light source, a modulated light source, a direct modulated source, an acoustic transducer, a piezoelectric acoustic transducer, an acoustic transducer air-coupled to a sample, an acoustic transducer liquid-coupled to the sample, a surface acoustic wave (SAW) generator, a surface acoustic wave (SAW) generator fluid-coupled to the sample, a surface acoustic wave (SAW) generator as at least part of the sample, a surface acoustic wave (SAW) generator configured as a sample holder, a surface acoustic wave (SAW) generator configured as a substrate, a thermal source, a pulsed thermal source, an electromagnetic source, a radio frequency (RF) source, a terahertz (THz) source, or a pulsed electro-magnetic source.

17. The method according to claim 13 further comprising:
performing detection of detects in at least one of (1) an electronic surface, (2) a semiconductor surface, (3) a metallic surface, (4) a combination of at least two of an electronic surface, a semiconductor surface, and a metallic surface, (5) an electronic circuit, (6) one or more detector materials, (7) one or more wafers used for electronic circuits, or (8) focal plane arrays.

18. The method according to claim 13 further comprising:
determining a source of defects in at least one of subsurface or surface images using a feedback loop; and
correcting for the defects in at least one of subsurface or surface images.

19. The method according to claim 13 further comprising:
at least one of:
   performing speckle reduction including using a coherent source in conjunction with at least one of a moving diffuser, a moving scattering media, and moving a multimode fiber; or
   performing speckle reduction including using an incoherent or a low coherence source and a narrow-wavelength-band filter.

20. A sensor comprising:
a plurality of imaging components for imaging a sample configured to perform (1) subsurface imaging by acoustical excitation and optical detection, and (2) interferometric surface topographic measurement, the plurality of imaging components including at least
   an image detector array;
   an acoustic excitation source configured to acoustically excite the sample to provide image information of a plurality of points of the sample;
   wherein the acoustic excitation source is a pulsed laser that propagates through free space;
   a stationary interferometric microscope having a speckle reduction device operatively connected to the interferometric microscope such that the interferometric microscope is configured to receive image information of the plurality of points of the sample from the image detector array; and
   a filter configured to separate the image information of the plurality of points of the sample into a surface component and a subsurface component.

21. The sensor according to claim 1 wherein:
at least one of the plurality of imaging components is configured for detection of delamination in semiconductor wafers;
the plurality of imaging components is configured for detecting defects in at least on of micro-electro-mechanical (MEMS) packaging or 3D MEMS;

the plurality of imaging components is configured for detecting at least one of cracks or delamination in semiconductor wafers;

the plurality of imaging components is configured for detecting defects in at least one of wafers, or substrates including at least one of voids, inclusions, or precipitates;

the plurality of imaging components is configured for detecting defects in focal plane arrays including at least one of voids, inclusions, or precipitates; or the plurality of imaging components is configured for detecting defects including at least one of cracks or voids in at least one of metals or metallization layers.

* * * * *